United States Patent
Hansis et al.

(10) Patent No.: US 11,571,138 B2
(45) Date of Patent: Feb. 7, 2023

(54) METHOD FOR CONFIGURING A MEDICAL DEVICE

(71) Applicant: KONINKLIJKE PHILIPS N.V., Eindhoven (NL)

(72) Inventors: Eberhard Sebastian Hansis, Muechen (DE); Michael Gunter Helle, Padenstedt (DE); Tim Philipp Harder, Ahrensburg (DE); Thomas Netsch, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 631 days.

(21) Appl. No.: 16/470,274

(22) PCT Filed: Dec. 18, 2017

(86) PCT No.: PCT/EP2017/083407
§ 371 (c)(1),
(2) Date: Jun. 17, 2019

(87) PCT Pub. No.: WO2018/114864
PCT Pub. Date: Jun. 28, 2018

(65) Prior Publication Data
US 2020/0008704 A1    Jan. 9, 2020

(30) Foreign Application Priority Data
Dec. 20, 2016   (EP) .................................... 16205244

(51) Int. Cl.
*G16H 40/63*    (2018.01)
*A61B 5/055*    (2006.01)
(Continued)

(52) U.S. Cl.
CPC .............. *A61B 5/055* (2013.01); *A61B 6/462* (2013.01); *A61B 6/545* (2013.01); *G16H 30/40* (2018.01);
(Continued)

(58) Field of Classification Search
CPC ......... A61B 5/055; A61B 6/462; A61B 6/545; A61B 5/0037; A61B 8/585; G16H 30/40; G16H 40/63; G16H 40/67; G01R 33/543
See application file for complete search history.

(56) References Cited

U.S. PATENT DOCUMENTS 10,267,879 B2    4/2019  Yokosawa et al.
2002/0151785 A1  10/2002 Mueller et al.
(Continued)

FOREIGN PATENT DOCUMENTS

WO    2015198680 A1   4/2017

OTHER PUBLICATIONS

International Search Report From PCT/EP2017/083407 dated Mar. 13, 2018.

*Primary Examiner* — Jason S Tiedeman
*Assistant Examiner* — Liza Tony Kanaan (57) ABSTRACT

The present disclosure relates to a method for configuring a medical device. The method comprises: providing a set of one or more parameters for configuring the medical device. Each parameter of the set has predefined values. A set of values of the set of parameters may be selected from the predefined values. Using the selected values the set of parameters may be set, which results in an operational configuration of the medical device. The medical device may be controlled to operate in accordance with the operational configuration, thereby an operating status of the medical device may be determined. Based on at least the operating status the operational configuration may be main- (Continued)

tained or the selecting, setting and controlling may be repeatedly performed until a desired operating status of the medical device can be determined based on the operating statuses resulting from the controlling.

20 Claims, 6 Drawing Sheets

(51) Int. Cl.
  *A61B 6/00* (2006.01)
  *G16H 30/40* (2018.01)
  *A61B 5/00* (2006.01)
  *G01R 33/54* (2006.01)
  *G16H 40/67* (2018.01)

(52) U.S. Cl.
  CPC ............ *G16H 40/63* (2018.01); *A61B 5/0037* (2013.01); *G01R 33/543* (2013.01); *G16H 40/67* (2018.01)

(56) References Cited

U.S. PATENT DOCUMENTS

| | | | |
|---|---|---|---|
| 2006/0058635 A1 | 3/2006 | Lehtonen-Krause | |
| 2009/0069668 A1* | 3/2009 | Stemmer | G06T 7/11 382/130 |
| 2010/0240992 A1* | 9/2010 | Hao | G01S 7/5205 600/437 |
| 2011/0066024 A1* | 3/2011 | Shih | G06T 7/0014 600/410 |
| 2013/0265044 A1 | 10/2013 | Senegas et al. | |
| 2013/0311472 A1 | 11/2013 | Cohen-Solal et al. | |
| 2014/0088984 A1 | 3/2014 | Oh et al. | |
| 2014/0129248 A1 | 5/2014 | Zuehlsdorff et al. | |
| 2015/0081315 A1 | 3/2015 | Baker | |
| 2015/0199478 A1* | 7/2015 | Bhatia | G06T 5/00 382/128 |
| 2016/0058426 A1* | 3/2016 | Hedlund | A61B 6/037 600/407 |
| 2016/0158438 A1* | 6/2016 | Monirabbasi | A61M 5/1723 604/67 |
| 2016/0310023 A1* | 10/2016 | Chachisvilis | A61B 5/0053 |

* cited by examiner

| | | | | | |
|---|---|---|---|---|---|
| Slice thickness (mm) | 4 | | Total scan duration | 01:00.0 | |
| Recon voxel size (mm) | 0.399 | | Rel. SNR | 0.709 | |
| Small FOV imaging | no | | Act. TR (ms) | 3000 | |
| Fold-over suppression | no | | Act. TE (ms) | 80 | |
| Restriction matrix | 576 | | ACQ matrix M x P | 420 x 270 | |
| SENSE ★ | yes (no) | | ACQ voxel MPS (mm) | 0.55 / 0.67 / 4.00 | |
| P reduction (RL) | range | | REC voxel MPS (mm) | 0.40 / 0.40 / 4.00 | |
| k-t BLAST | Minimum | 1.5 | Scan percentage (%) | 81.3 | |
| Stacks | Maximum | 2.2 | Packages | 2 | |
| type | parallel | | Min. slice gap (mm) | 4 | |
| slices | 28 | | WFS (pix) / BW (Hz) | 2.583 / 168.1 | |
| slice gap | user defined | | TSE es / shot (ms) | 10.0 / 150 | |
| gap (mm) | 1 | | TEeff / TEequiv (ms) | 80 / 72 | |
| slice orientation | transverse | | Min. TR (ms) | 2759 | |
| fold-over direction | RL | | SAR / local torso | < 92 % | |
| fat shift direction | P | | Whole body / level | < 3.0 W/kg / 1st level | |
| Minimum number of pa.... | 1 | | SED | < 0.2 kJ/kg | |

322 — Slice thickness (mm)
322 — Recon voxel size (mm)
322 — Small FOV imaging

FIG. 4

# METHOD FOR CONFIGURING A MEDICAL DEVICE

CROSS REFERENCE TO RELATED APPLICATIONS

This application is a U.S. national phase application of International Application No. PCT/EP2017/083407 filed on Dec. 18, 2017 which claims the benefit of EP Application Serial No. 16205244.3 filed on Dec. 20, 2016 and is incorporated herein by reference.

FIELD OF THE INVENTION

The invention relates to medical devices and procedures, in particular to a method for configuring a medical device.

BACKGROUND OF THE INVENTION

Modern medical devices like imaging devices have a large number of parameters that need to be adjusted for optimum operation. One example are magnetic resonance (MR) imaging machines, which offer a large number of acquisition parameters that influence the final image characteristics. Improving the performance of such medical devices based on the parameters may be a complicated and time-consuming task.

SUMMARY OF THE INVENTION

Various embodiments provide for a method for configuring a medical device, control system, and computer program product, as described by the subject matter of the independent claims. Advantageous embodiments are described in the dependent claims.

In one aspect, the invention relates to a method for configuring a medical device. The method comprises: providing a set of one or more parameters for configuring the medical device. Each parameter of the set has predefined values. A set of values of the set of parameters may be selected from the predefined values. Using the selected values the set of parameters may be set, which results in an operational configuration of the medical device. The medical device may be controlled to operate in accordance with the operational configuration, thereby an operating status of the medical device may be determined. Based on at least the operating status the operational configuration may be maintained or the selecting, setting and controlling may be repeatedly performed until a desired operating status of the medical device can be determined based on the operating statuses resulting from the controlling. Parameters for configuring the medical device could for example be image resolution, echo time (TE), repetition time (TR), slice thickness, SENSE factor, flip angle, inversion time, fat/water relation, frequency bandwidth, frequency and phase encoding direction, number of averages etc.

Embodiments of the invention relate to incorporating parameter optimization as an ongoing task in the normal device operation. A user sets a range or ranges for a single configuration parameter or a set of parameters to be evaluated, preferably defined in such a way that normal device operation and usage is not or only limitedly affected. This is achieved by selecting different parameter sets from the ranges for different patients, which are scheduled for a diagnostic MRI. In this way, parameter or protocol optimization can be integrated in the standard clinical workflow. For each use, parameter sets are selected (e.g. randomly) from the provided range or ranges. When reviewing the outcome, e.g. the acquired medical images, the user is supplied with a simple feedback mechanism to judge outcome quality, e.g. the image quality. Based on the feedback, after the acquisition of data from multiple patients, a favourable parameter set can be selected from the defined parameter ranges. In this way, (blind randomized) micro-trials for parameter optimization can be integrated in the normal workflow. The favourable parameter set can then later be used on future, similar patients, e.g. similar in terms of body part, age, gender, weight and/or clinical question A desired operating status of the medical device can be determined based on the operating statuses resulting from the controlling. For example, if the number of operating statuses (which corresponds to the number of iterations) is high enough this may enable to find a desired operating status among the operating statuses resulting from the controlling. The desired operating status may be determined by for example selecting the best operating status among the operating statuses resulting from the controlling. In another example, the desired operating status may be determined by fitting a statistical model to the operating statuses resulting from the controlling in combination with their respective selected set of values.

In one example, if in a current iteration the operating status is a desired operating status the operational configuration of the current iteration may be maintained e.g. as being an optimal configuration.

In another example, the desired operating status may be obtained by comparing the operating statuses of a predefined number of iterations and selecting among them the optimal operating status. The selected set of values of the set of parameters that provides the optimal operating status can be used to set the set of parameters to obtain the optimal configuration of the medical device.

In a further example, the desired operating status may be determined by generating an optimal set of values out of the sets of selected values of the predefined number of iterations. For example, the method may be repeated until the number of iterations reaches the predefined number of iterations e.g. 3 iterations. The three iterations result in three sets of selected values. By combining the three selected sets of values and corresponding operating statuses an optimal set of values that corresponds to a desired operating status may be obtained. The optimal set of values may be used to set the set of parameters to obtain the optimal configuration. The combination may for example comprise fitting regression models to the three sets of values of the set of parameters and base the selection of the optimal set of values of the set of parameters on the model.

The first iteration is or refers to the first execution of the method steps (e.g. the selecting, setting and controlling steps).

The operational configuration may be maintained based on at least the operating status and the number of iterations. For example, if the number of iterations is smaller than a predefined number of iterations, the operational configuration may not be maintained. In case, the current number of iterations is higher than one, the maintaining or rejecting of the operational configuration may be based on the operating statuses determined for each iteration of the iterations.

The term "medical device" as used herein refers to a medical diagnostic device for performing a medical diagnosis and/or to a medical therapeutic device for delivering a treatment. The medical device is a processor controlled device. For example, the medical device is configurable by a processor based device. The medical device has a number of settings that can be modified such that the medical device can operate in accordance with the settings.

The medical diagnostic device may for example comprise a medical imaging device.

The treatment may for example comprise a drug, active therapy, tests or surgery. Active therapy comprises at least one of, radiation therapy, chemotherapy, anesthesiology, laser therapy, light therapy and other anatomically altering therapy, for example.

The set of parameters may be a subset of a larger set of parameters. For example, the medical device may be configurable by N parameters. The set of parameters may comprise a number of parameters that is smaller or equal to N. The set of parameters may for example be selected from the larger set. The selection of the set of parameters may be a random selection. In another example, the set of parameters may be selected by a user of the medical device. In one example, the method may be repeated (for parameter optimization) for the remaining parameters of the largest set that are not part of the set of parameters. This may enable an optimization of the parameters in chunks.

Each parameter of the set of parameters may be set by a constant value. The constant value of a parameter may be derived or selected from predefined values of the parameter. The predefined values may be discrete values or a range of values. For each parameter of the set of parameters, values may be defined. For example, for a given parameter of the set of parameters one or more values or ranges of values may be defined.

For example, a database may be provided where each parameter of the set of parameters is associated with its predefined values. Having multiple predefined values for each parameter of the set of parameters may enable finding the most optimal operational configuration of the medical device. In one example, the predefined values of at least part of the set of parameters may be time and/or location dependent. For example, a parameter of the set of parameters may be associated with different values for different time periods and/or different locations. For example, a monitor monitoring the physiological state of a patient may have different settings depending on the time of day, e.g. setting different limits for alarms at nighttime than at daytime. In another example, the predefined values of a location dependent parameter may be provided based on the location of the medical device. For example, if the medical device is located in England a temperature parameter may be configured in Fahrenheit units while in Germany the temperature parameter may be configured in Celsius units.

The operational configuration of the medical device may be defined by setting values for at least the set of parameters. For example, if the set of parameters is a subset of the larger set of parameters, the remaining parameters of the larger set may be fixed and the method may be applied in order to optimize the set of parameters while the remaining parameters are set to fixed values.

The operating status of the medical device may be defined by one or more operating parameters of the medical device. The operating parameters may be descriptive of the operation of the medical device. The operating parameters of the medical device may indicate the functional requirements of the medical device such as the response time of the medical device. For example, determining the operating status of the medical device may comprise evaluating the operating parameters.

A safe operation may be guaranteed by setting the predefined values of the set of parameters within a certain range.

The present method may for example avoid setting the parameters once at the initial setup of the medical device without further optimizations. The present method may enable a systematic parameter optimization.

The present method may enable optimizing multiple parameters at a time. This is by contrast to a complicated and time-consuming task, requiring changing one parameter at a time and evaluating its influence. The present method of optimizing the parameters may be an ongoing task in the normal medical device operation e.g. while a patient is treated by the medical device.

Non limiting examples of a parameter of the set of parameters include: in case of an ultrasound imaging system the set of parameters may comprise penetration depth, frequency range and dynamic range. In case of an electrocardiographic monitor the set of parameters may comprise sampling rate, input impedance, ECG signal measurement range. In case of an infant warmer the set of parameters may comprise heater power switch range, patient temperature range control, temperature resolution, maximum heater power output.

According to one embodiment, the controlling of the medical device results in output data of the medical device. The determining of the operating status comprises evaluating at least one predefined metric and comparing the evaluated metric with a predefined threshold or with a predefined criterion. The criterion may for example maps values of the metric to corresponding ratings that indicate operating statuses and using the map to identify the rating for the evaluated metric. In one example, the threshold may comprise a reference value. The reference value may be the value of the metric that is determined for the medical device before starting the present method for optimizing the set of parameters. By comparing the metric value with the reference value it may be determined whether the operating status of the medical device is improved (e.g. response time becomes shorter). In another example, the threshold may comprise the metric value of a previous iteration. The previous iteration may be the iteration that immediately happened before the current iteration. The comparison of the metric with the threshold may indicate the operating status of the medical device. For example, if the evaluated metric corresponds to expected values this may indicate a normal operation of the medical device that is not impeded. This embodiment may enable a systematic way for automatically validating or rejecting chosen values of the set of parameters.

According to one embodiment, the metric comprises at least one of: processing time (or response time) of the medical device for performing the operation; matching level of the output data and predefined reference data; user rating of the output data and one or more operating parameters of the medical device.

An operating parameter of the medical device characterizes the operation of the medical device. Non-limiting examples of the operating parameter include: response time, processing time, measurement accuracy (e.g. measurement accuracy of an ultrasound imaging system that is to be better than 2% over 10 cm distance may indicate a desired operating status of the medical device being the ultrasound imaging system), effectiveness (a medical device is clinically effective when it produces the effect intended by the manufacturer), image quality of the medical device being a medical imaging device (the image quality may be user defined or automatically evaluated), noise and contrast resolution of the medical imaging device, stability of operation (in what fraction of cases is the operation effective and does not require intervention by an operator of the medical device), limiting harm or risk to the patient (e.g. reduction in the amount of ionizing radiation applied by the medical imaging device or a radiotherapy system).

According to one embodiment, the method further comprises providing a visual indication of the operating status and receiving a user input indicative of the maintaining of the operational configuration or of performing the repetition. The user may provide feedback on the displayed operating status. This may enable a faster convergence of the present method as the user may tolerate some features of the operation of the medical device that may not automatically be possible. For example, if a value of the operating parameter is smaller than a threshold (even if the difference between the operating parameters and the threshold is very small) the method may automatically determine that the operating status is not the desired one. However, the user may accept the operating status as the desired one because the difference between the operating parameters and the threshold is very small.

In another example, the method further comprises ranking the operating statuses obtained in each iteration of selecting, setting and controlling steps (e.g. "excellent" rating may be ranked first, "very good" rating is second ranked and so on), selecting the first ranked operating status, providing a visual indication of the selected operating status and receiving a user input indicative of the maintaining of the operational configuration that provided the selected operating status or receiving an indication for repeating the selecting, setting and controlling steps. The user may not be happy with a "good" rating and may thus request to repeat the method e.g. to obtain an "excellent" rating.

According to one embodiment, the controlling of the medical device results in multiple outputs of the medical device, wherein the operating status is determined for each of the multiple outputs. The multiple outputs may result from repeating the operation of the medical device multiple times using the same values of the set of parameters. The repetition using the same values of the set of parameters may be advantageous as it enables to gain a statistical certainty about the resulting operating status. The repetition is performed in response to detecting a variation in the operating statuses. For example, the multiple outputs may result from repeating the operation of the medical device multiple times with the same set of parameters and the selected values. If the operating status changes for two different outputs this may be an indication of instability of the medical device and thus the operational configuration may not be maintained and has to be defined again as described above. This embodiment may provide a reliable and robust operational configuration of the medical device compared to the case where a single output is used to decide on maintaining or not the operational configuration.

According to one embodiment, the controlling of the medical device results in multiple outputs of the medical device, wherein the operating status is determined for each of the multiple outputs. The multiple outputs may result from repeating the operation of the medical device multiple times using the same values of the set of parameters. The method further comprises rating each of the operating statuses based on a predefined metric, and performing the maintaining or the repetition based on the ratings. The rating may reflect the operating status. The multiple outputs may result from repeating the operation of the medical device multiple times with the same set of parameters and the selected values. For example, assuming the operating status is defined by the response time of the medical device. The rating may be "good" if the response time is smaller than 3 min and "bad" if the response time is higher than 3 min. The ratings of the multiple outputs may indicate the number of times "good" is found and the number of times "bad" is found. In case the fraction of "good" ratings has increased compared to the same fraction obtained with a different set of values of the set of parameters (e.g. the parameters used before the optimization was started) the operational configuration may be maintained.

The medical device may be a medical imaging device. According to one embodiment, the medical device is selected from the group consisting of MRI, CT, Ultrasound, Radiography, and PET imagers.

According to one embodiment, the controlling of the medical device comprises: acquiring MRI data; reconstructing one or more MR images using the acquired MRI data. The determining of the operating status comprises evaluating the acquisition time and/or an image quality metric of the reconstructed MR images, comparing the evaluated acquisition time and/or image quality metric with predefined thresholds. The comparision may be performed in order to detect improvements in the operation of the medical device. For example, the thresholds may comprise reference values of the metric (e.g. measured before starting the evaluation).

According to one embodiment, the acquisition of the MRI data is performed using a predefined parallel imaging technique, wherein the image quality metric comprises a contrast metric.

According to one embodiment, the method further comprises determining the predefined values. The determining of the predefined values comprises: collecting the predefined values from one or more other medical devices similar to the medical device; or using simulation data that is obtained from a simulation of the medical device based on a model of the medical device; or using user inputs to define valid parameter ranges; or obtaining parameter ranges from specifications supplied by the manufacturer of the medical device. This may enable a faster convergence of the present method in contrast to randomly changing the values of the set of parameters using theoretically defined values. In addition, this embodiment may ensure a safe and effective operation of the medical device. The set of parameters may be set such that regular device operation may be guaranteed, since the optimization of the set of parameters may to be carried out during normal operation on patients.

According to one embodiment, the predefined values are user defined values. An expert may provide valid ranges and/or the set of parameters to be evaluated, defined in such a way that normal device operation and usage is not impeded.

According to one embodiment, the set of parameters comprises image acquisition and/or image reconstruction parameters.

In another aspect, the invention relates to a computer program product comprising machine executable instructions for execution by a processor, wherein execution of the machine executable instructions causes the processor to the methods of preceding embodiments.

In another aspect, the invention relates to a control system for a medical device, the control system comprising a processor, and a memory containing machine executable instructions, wherein execution of the instructions causes the processor to: select from predefined values a set of values of a set of one or more parameters; set the set of parameters using the selected set of values, resulting in an operational configuration of the medical device; control the medical device to operate in accordance with the operational configuration, thereby determining an operating status of the medical device; based on the operating status maintain the operational configuration or repeatedly performing the selecting, setting and controlling until a desired operating status of the medical device is determined based on the operating statuses resulting from the controlling.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figures are either similar elements or perform an equivalent function. Elements which have been discussed previously will not necessarily be discussed in later figures if the function is equivalent.

Various structures, systems and devices are schematically depicted in the figures for purposes of explanation only and so as to not obscure the present invention with details that are well known to those skilled in the art. Nevertheless, the attached figures are included to describe and explain illustrative examples of the disclosed subject matter.

Figure 1:
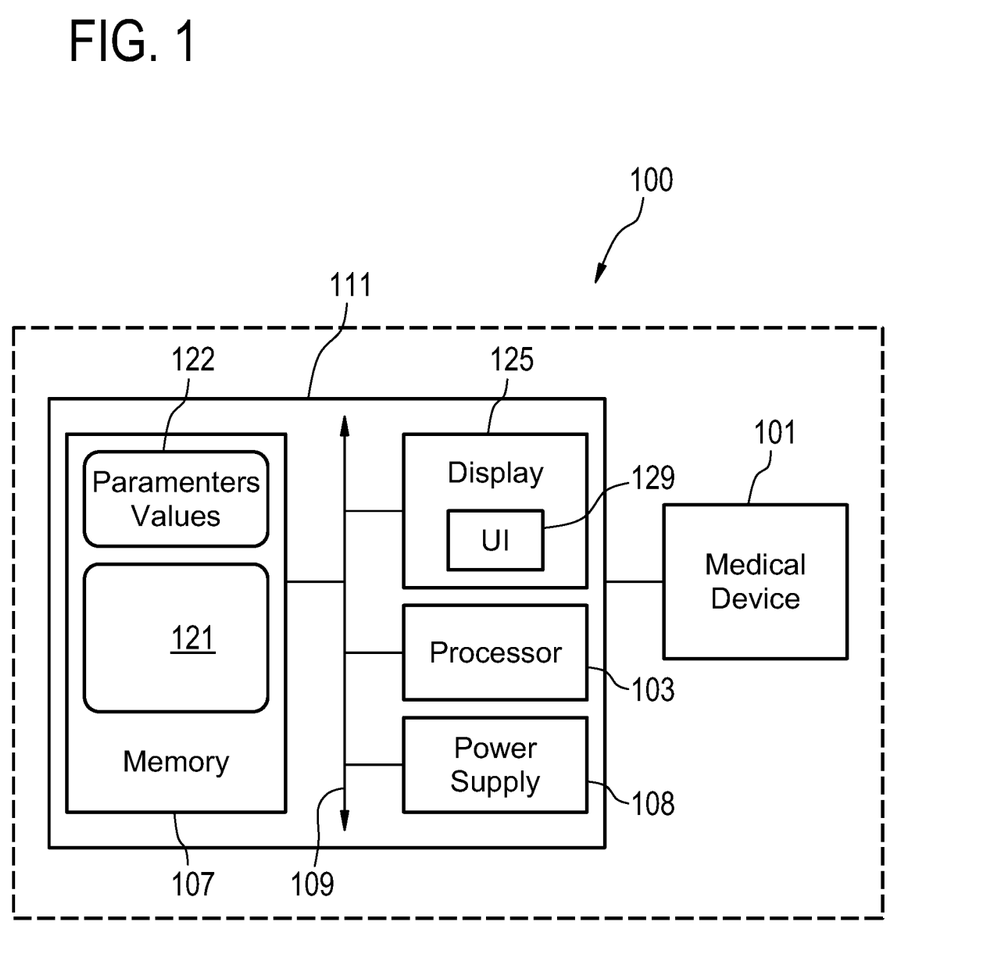
FIG. 1 is a schematic diagram of a medical system.

FIG. 1 is a schematic diagram of a medical system 100. The medical system 100 comprises a control system 111 that is connected to a medical device 101. The medical device 101 may be a processor controlled device. The control system 111 comprises a processor 103, a memory 107 each capable of communicating with one or more components of the medical system 100. For example, components of the control system 111 are coupled to a bidirectional system bus 109.

It will be appreciated that the methods described herein are at least partly non-interactive, and automated by way of computerized systems. These methods can further be implemented in software 121, (including firmware), hardware, or a combination thereof. In exemplary embodiments, the methods described herein are implemented in software, as an executable program, and is executed by a special or general-purpose digital computer, such as a personal computer, workstation, minicomputer, or mainframe computer.

The processor 103 is a hardware device for executing software, particularly that stored in memory 107. The processor 103 can be any custom made or commercially available processor, a central processing unit (CPU), an auxiliary processor among several processors associated with the control system 111, a semiconductor based microprocessor (in the form of a microchip or chip set), a macroprocessor, or generally any device for executing software instructions. The processor 103 may control the operation of the medical device 101.

The memory 107 can include any one or combination of volatile memory elements (e.g., random access memory (RAM, such as DRAM, SRAM, SDRAM, etc.)) and non-volatile memory elements (e.g., ROM, erasable programmable read only memory (EPROM), electronically erasable programmable read only memory (EEPROM), programmable read only memory (PROM). Note that the memory 107 can have a distributed architecture, where various components are situated remote from one another, but can be accessed by the processor 103. Memory 107 may store an instruction or data related to at least one other constituent element of the medical system 100.

The control system 111 may further comprise a display device 125 which displays characters and images and the like e.g. on a user interface 129. The display device 125 may be a touch screen display device.

The medical system 100 may further comprise a power supply 108 for powering the medical system 100. The power supply 108 may for example be a battery or an external source of power, such as electricity supplied by a standard AC outlet.

The medical device 101 may comprise a therapeutic device for treatment delivery and/or a diagnostic device. The control system 111 and the medical device 101 may or may not be an integral part. In other terms, the medical device 101 may or may not be external to the control system 111.

The medical device 101 comprises components that may be controlled by the processor 103 in order to configure the medical device 101. The configuration of the medical device 101 may enable the operation of the medical device 101. The operation of the medical device 101 may or may not be automatic.

Figure 4:
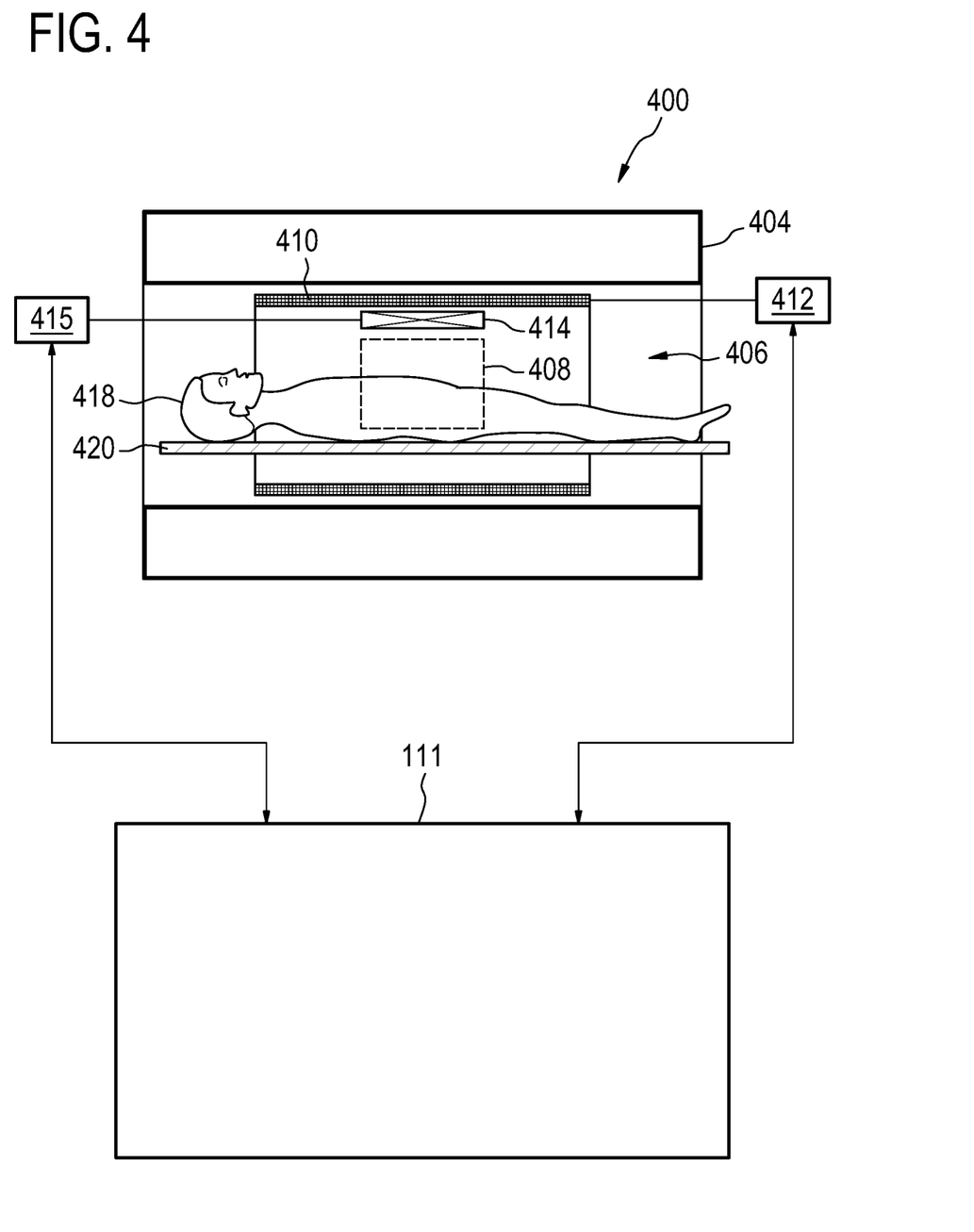
FIG. 4 shows a cross-sectional and functional view of an MRI system.

In one example, the medical device 101 may comprise an integrated circuit having components that enable the medical device 101 to be configured in order to function. For example, the integrated circuit may comprise a microprocessor, memory, analog front end, power management section and a communication section for communication with the control system 111. The microprocessor and the memory may not be necessary in case the medical device 101 is an integral part of the control system 111. FIG. 4 shows another example of components of the medical device 101.

The connection between the control system 111 and the medical device 101 may for example comprise a BUS Ethernet connection, WAN connection, Internet connection etc.

The medical device 101 may have a number of settings that can be modified or set or controlled by the processor 103. These settings may form part of register contents that control the function of the medical device 101. The settings may comprise a set of one or more parameters 122 whose values may be stored in the memory 107.

The set of parameters 122 may be specifications of the medical device 101 such as technical specifications of the medical device 101 which can be used for configuration of the medical device 101.

In one example, the medical device 101 may be configured to provide output data in response to a specified measurement e.g. by a sensor. In another example, the medical device 101 may be configured to provide a therapy. The configuration of the medical device 102 may be performed by the processor 103. For example, the processor 103 may be configured to establish the register contents of the medical device 101 that can be used to configure the medical device 101.

The processor 103 may be adapted to receive information from the medical device 101 in a compatible digital form so that such information may be displayed on the display device 125. Such information may include operating parameters, alarm notifications, and other information related to the use, operation and function of the medical device 101.

In one example, the medical device 101 may be configured to receive and/or send data from or to a source (e.g. 111) and to use the data to perform the diagnostic and/or deliver the treatment. In another example, the medical device 101 may display its operational status and output data to the user on an integrated display of the medical device 101.

The medical device 101 may be in communication with one other medical devices (not shown) e.g. via a network. For example, the values of the set of parameters 122 may be received from the other medical devices.

The operating parameters may be used to determine an operating status of the medical device 101.

Figure 2:
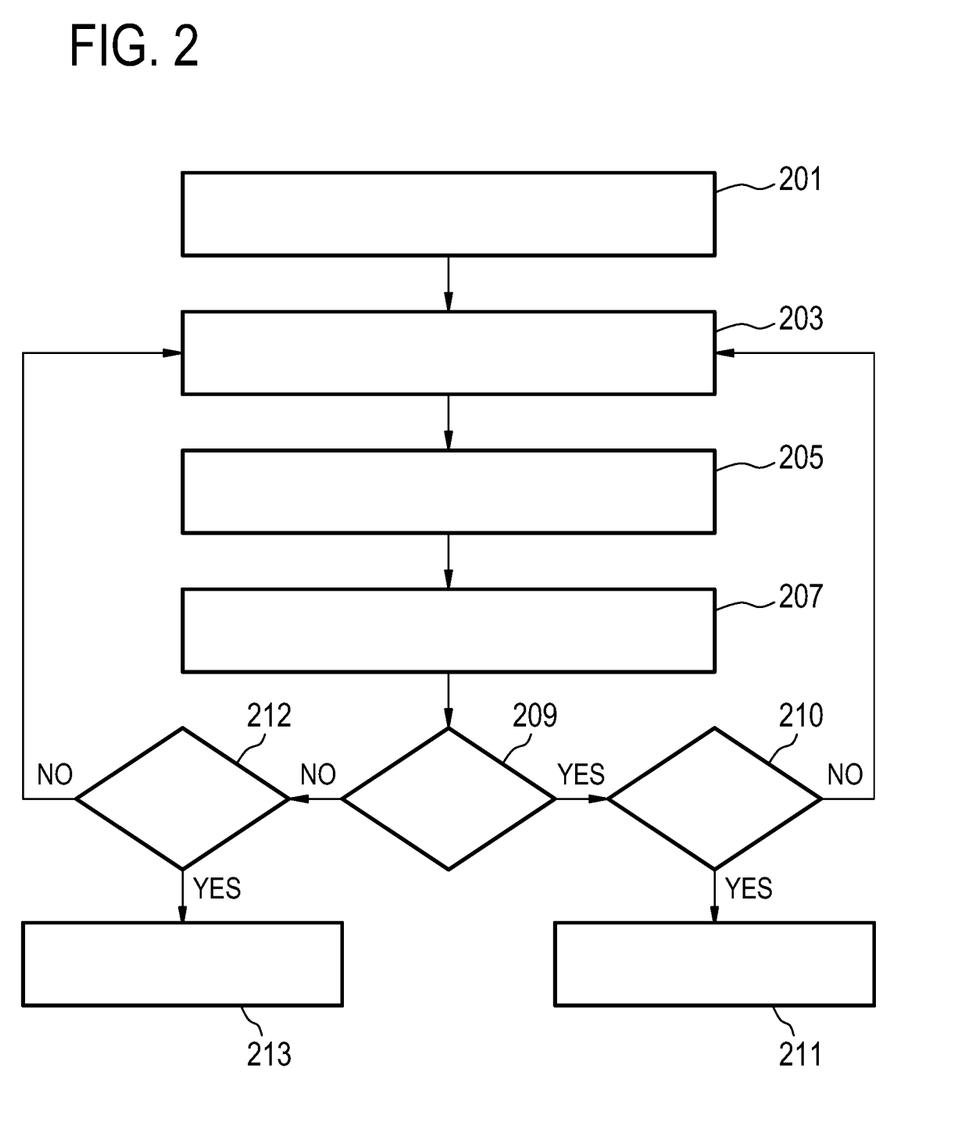
FIG. 2 is a flowchart of a method for configuring a medical device.

FIG. 2 is a flowchart of a method for configuring a medical device e.g. 101. The medical device 101 may be configurable using set of parameters 122.

In step 201, values of the set of parameters 122 may be provided. For example, for each parameter of the set of parameters a range of values or discrete values may be provided or defined. The values of the set of parameters 122 may be optimal values for operation of the medical device 101. Assuming for example that the set of parameters comprise par1 and par2, where par1 can be set by range of values and par2 can be set by a constant value. In this case, the values to be provided may for example comprise a pair (v1, v2) . . . as a value range for par1 (e.g. par1 can vary from v1 to v2) and constant values l1, l2, l3 etc. for par2 (e.g. par2 may have value l1).

For example, the values of the set of parameters 122 may be user defined. The user can be supported when entering parameter ranges by supplying him with pre-defined safe or recommended parameter ranges. In another example, the values of the set of parameters 122 may be determined using simulation data that is obtained from a simulation of the medical device 101 based on a model of the medical device. Additional information can be gained from a simulation module which (approximately) simulates the effect of certain parameter settings on the output data of the medical device 101.

In another example, values of the set of parameters may be collected from one or more other medical devices similar to the medical device 101. The values of the set of parameters 122 may be collected from other uses (e.g. of the other medical devices) and exchanged via a cloud-based collaboration system. For example, an MR system operator may choose to copy acquisition parameters shared by other institutions e.g. via the cloud-based collaboration system.

In step 203, a set of values may be selected from the predefined values of step 201. The set of values are respective values of the set of parameters 122. Using the above example of par1 and par2 the set of values may for example comprise a value between v1 and v2 for par1 and l2 for par2.

In one example, the set of values may be randomly selected e.g. for each use of the medical device. This may be 'true' random selection or a different sampling mechanism like shuffled step-wise scanning of a parameter range. If multiple parameters are to be optimized, parameter selection may entail sampling methods to optimize coverage of a multi-dimensional parameter space. Parameter optimization may be limited to certain use cases of the medical device 101 (e.g. certain scanned anatomies) or protocols.

In step 205, the medical device 101 may be configured by setting the set of parameters 122 using the selected set of values. The setting of the set of parameters 122 may result or may define an operational configuration of the medical device 101.

In one example, each of the set of parameters 122 may be set to the respective one or more values of the selected values. In another example, the selected values may be adapted such that they can be set to the respective set of parameters. The adaptation may for example be performed based on a model that extrapolates the selected values. If for example, the selected values lead to a desired operating status e.g. having a rating "good", the model may adjust or extrapolate the values such that the rating may be higher e.g. "excellent". The adaptation or the extrapolation may be performed using reference data indicative of the set of parameters and/or previous selected values.

Using the above simplified example of par1 and par2, if the set of values selected comprises v1 for par1 and l2 for par2, par1 is set to v1 and par2 is set to l2 or par1 is set to v1+-delta and par2 to l2, where delta is a predefined value etc.

In step 207, the medical device 101 may be controlled to operate in accordance with the operational configuration, thereby determining an operating status of the medical device 101. The operating status may be determined by determining a rating (or quality rating) indicative of the operation of the medical device. The rating may be calculated based on output data and/or on the operation of the medical device. For example, a rating may be calculated based on the response time of the medical device. In another example, the rating may be calculated based on the quality of the output data such as images. The rating may for example be "excellent", "good", "moderate" or "not acceptable", e.g. if the response time is smaller than Xmin the rating may be "excellent".

The control of the medical device 101 may result in output data of the medical device 101. The output data may for example comprise the operating parameters as described above. The operating status may be determined by evaluating at least one predefined metric and by comparing the evaluated metric with a predefined threshold. The metric may for example be determined using one or more the operating parameters. For example, the metric may be calculated as the difference between the value of an operating parameter with a predefined reference value of that operating parameter. The difference may be compared with the predefined threshold. If the difference is too high this may be indicative of a non-desired operating status. In another example, the difference may be indicative of an improvement in the operation of the medical device. The operating status may for example be represented by a variable e.g. a Boolean variable, indicating whether the operating status is a desired status (e.g. value 1) or a non-desired operating status (e.g. value 0).

In one example, the control of the medical device 101 in step 207 may comprise repeating the operation or the usage of the medical device multiple times using the same selected values of the set of parameters. This may result in multiple ratings as described above for each repetition. In this case, the multiple operation of the medical device may result in multiple output data that can be compared in order to decide whether the operating status of the medical device is the desired one or not. For example, if the operating status changes from one output data to another output data this may be an indication that the operating status of the medical device is not stable and thus it may not be the desired one. In another example, if the fraction of "excellent" rating of the multiple ratings is higher than a predefined threshold this may indicate that the operating status of the medical device is the desired one. The threshold may for example comprise the fraction of "excellent" ratings obtained in a previous iteration or obtained in a separate previous operation of the medical device 101.

In another example, the operating status of the medical device 101 may be determined using the current operating status and previously determined operating statuses in the previous iterations. For example, the ratings of the iterations may be combined to provide the fraction of each rating type which would be an indication of the operating status of the medical device.

In case the current iteration (inquiry 209) is the first iteration (the first iteration refers to the first or initial execution of the steps 203-207) determining if the operating status (inquiry 210) is a desired operating status, and if so the operational configuration may be maintained in step 211, otherwise steps 203-207 may be repeated. The maintained operational configuration may be used for further or future usage of the medical device 101.

In case the current iteration (inquiry 209) is not the first iteration, determining if (inquiry 212) a desired operating status can be determined using at least part of the operating statuses so far determined for each iteration. For example, the determined operating status of each iteration may be saved. If a desired operating status can be determined, the set of values that enables the desired operating status may be provided in step 213; otherwise steps 203-207 may be repeated. The provided values of the set of parameters in step 213 may be used for further or future usage of the medical device 101.

The inquiry 212 may for example comprise a condition on the number of repetitions that has to be fulfilled. For example, if the number of repetitions is smaller than a predefined number of repetitions the desired operating status cannot be determined. The predefined number of repetitions may guarantee a reliable determination of the operating status. For example, the combination of the data from the repetitions may be enough to conclude on a set of values that corresponds to the desired operating status.

In another example, inquiry 212 may comprise comparing the operating statuses obtained so far from the iterations and selecting the best operating status (e.g. the first ranked as excellent as described above), and comparing the selected operating status with a desired operating status, wherein if the comparison fails (they are not the same) this means that the desired operating status cannot be determined and steps 203-207 has to be repeated.

In one example, inquiry 210 may comprise prompting a user of the medical device 101 for providing input data (feedback) indicating if the operating status is a desired operating status. The operating status may for example be indicated by acquired images of the medical device, in case of a medical imaging device. When reviewing the outcome, e.g. the acquired medical images, the user may be supplied with a feedback mechanism to judge outcome quality, e.g. the image quality. The feedback may indicate of the operating status is a desired one or not. Based on the feedback that the operating status is the desired one, the corresponding optimum parameter set can be selected from the defined parameter ranges.

For example, ratings that indicate the operating statuses of each iteration may be saved and the selected values of step 203 (tested parameter set) of each iteration may be also saved. For a given iteration, inquiry 212 may comprise based on the combination of ratings and tested parameter sets (so far saved), the optimum parameter set may be extracted from the prescribed parameter range. If the optimum parameter set can be extracted the desired operating status can be determined using the optimum parameter set. This may include detection of the maximum score, fitting and evaluation of statistical models, or other methods. The selection may include the estimation of confidence intervals for the parameters and statistical significance of the evaluation result. The resulting optimized parameter set (which defines the operational configuration of the medical device) can be shown to the user and saved to the system for future use.

For example, assume that the set of parameters comprises a single parameter that can take on values within a certain range. The value of the parameter may be selected as a sample by sampling the range e.g. in five equally spaced points or by selecting a random value within the range. For each tested value the operating status may be determined (e.g. a contrast-to-noise ratio may be evaluated). Each iteration may be represented as a data point having a pair [parameter value, operating status]. By fitting a smooth function through these data points an optimum value may be found. For example, if the contrast-to-noise ratio is low for very small and very large parameter values and larger for medium parameter values, a bell-shaped curve may be fitted to the data points. The maximum of that curve will lie within the range of tested values of the parameter. More generally, regression models may be fit to one or several set of values of the set of parameters and base the parameter selection on the model.

In case of a medical imaging device, the optimization may take into account patient and disease specific data like the patients' age or size. For example, one may fit a regression model that takes into account the value of the modified parameter as one variable, the weight of the patient as a second variable, and the measured outcome as the result. This way, rules may be derived for setting parameters that take into account the patient weight, e.g. set a parameter differently for small patients than for large patients. As another example, different optimum parameters may be derived for patients with different clinical boundary conditions (disease, comorbidities, . . . ) or for different diagnostic questions.

The optimization outcome of the present method may be reported back to the peers or to the parameter exchange cloud solution.

The present method e.g. steps 203-213 may be performed on a regular basis e.g. every month or week. This may enable to take into account the evolution of the medical device 101.

Figure 3A:
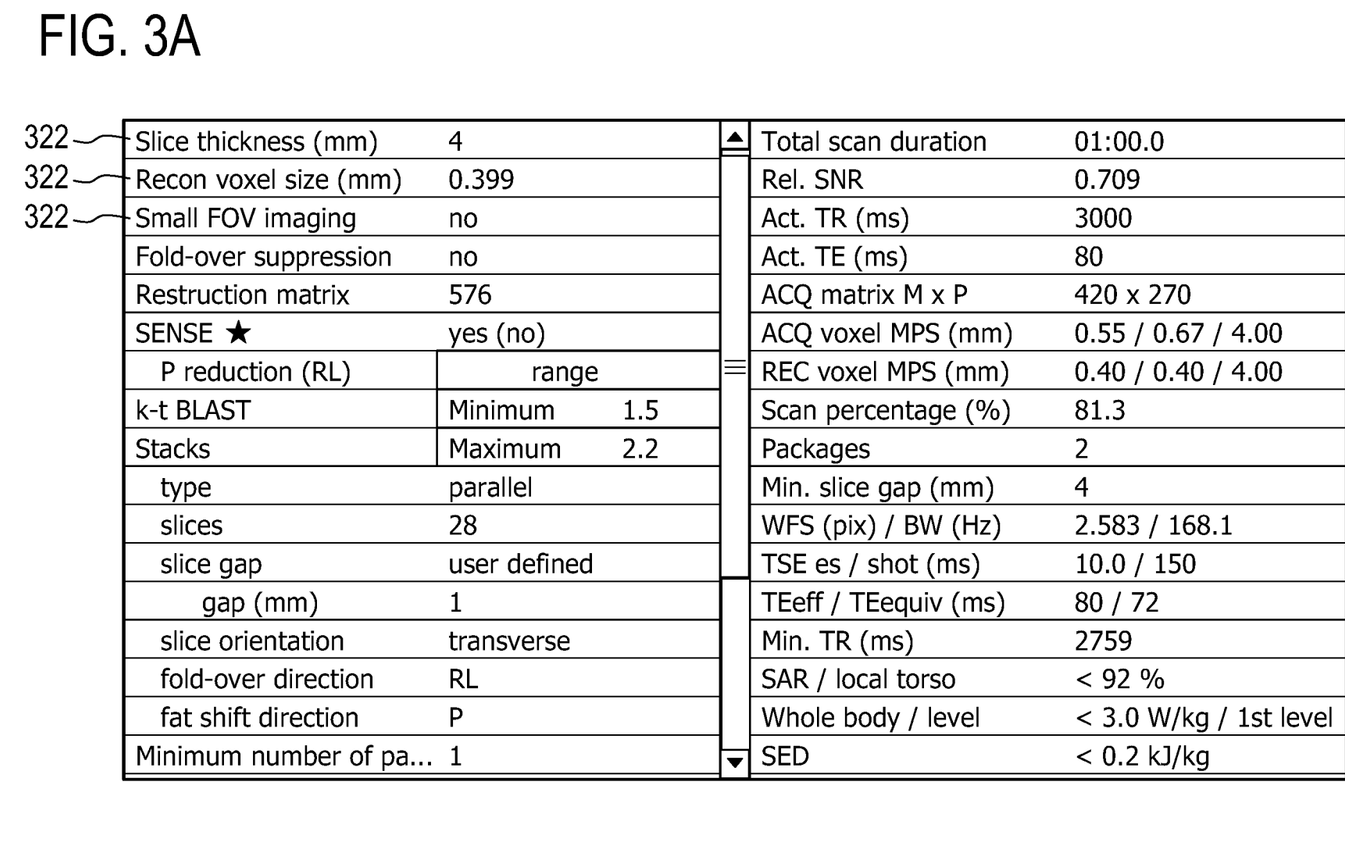
FIGS. 3A-3C illustrates a method for determining the desired operating status of the medical device being an MRI system.
Figure 3B:
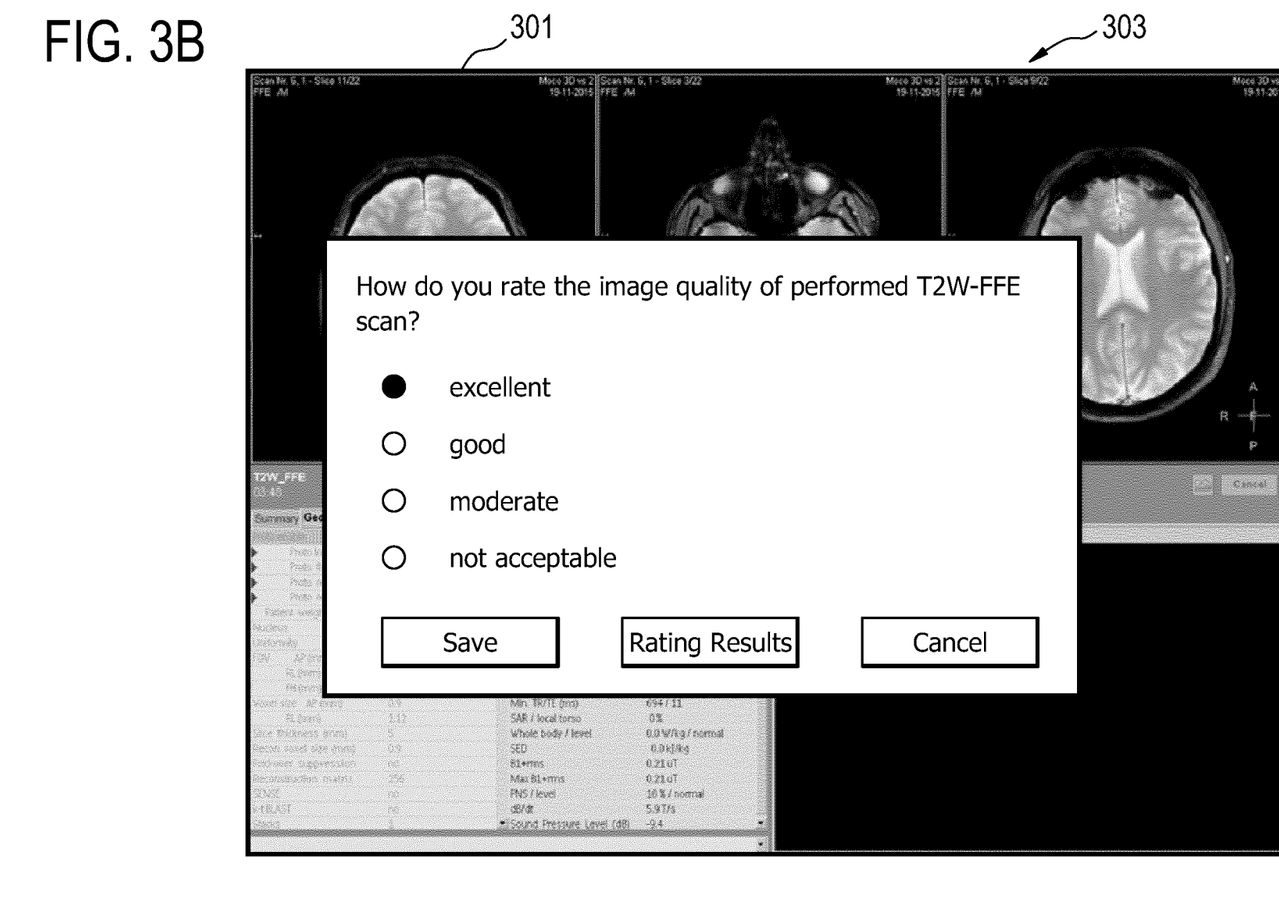
Figure 3C:
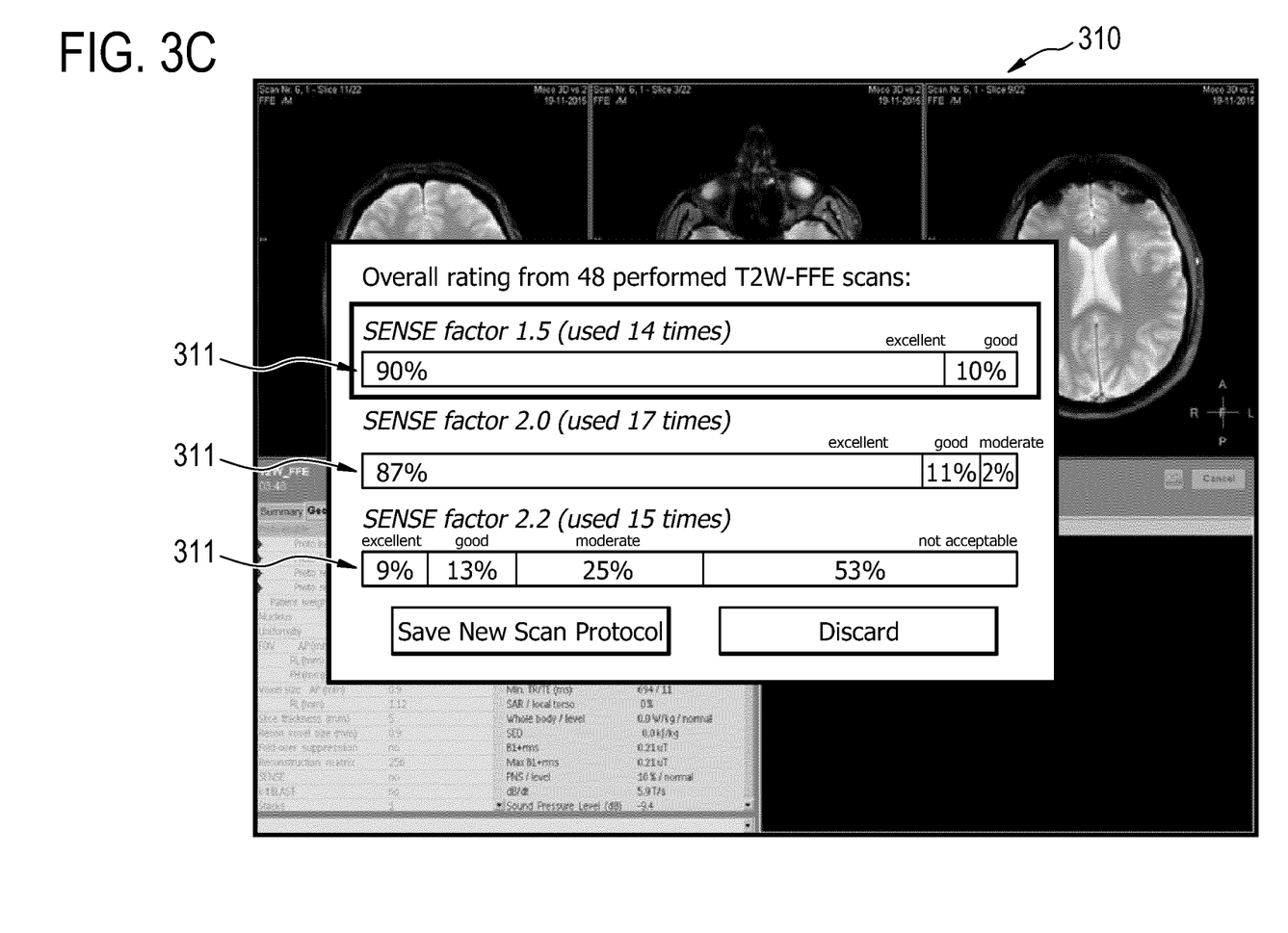

FIGS. 3A-3C illustrates a method for determining the desired operating status of a medical device 101 being a MRI system as described with reference to FIG. 4. FIG. 3A may for example be displayed while performing steps 203 and 205 of FIG. 2.

FIG. 3A shows set of parameters 322 that can be used to configure the MRI system in order to acquire MR data. The set of parameters 322 may for example be displayed on the graphical user interface 129 such that the user may enter values of the set of parameters 322. For example, an expert may enter valid parameter ranges for the sets of parameters to be evaluated enabling options for setting the parameters 322. For each use or operation of the medical device, a parameter set may randomly be selected from these options.

For example, the user may aim to use the medical device in order to reduce the acquisition time for T2-weighted MRI scans by using SENSE, without changing other parameters like image resolution or slice number.

As shown in FIG. 3A, parameters 322 may be set to respective values. A parameter can be set to a constant value or to a range of values. For example, the slice thickness parameter is set to a value of 4 mm and SENSE factor parameter is set to a range of values from 1.5 to 2.2.

The parameters (such as set of parameters 122) to be investigated or optimized among the larger set of parameters 322 can for example be marked with a star as illustrated in FIG. 3A such that the user can enter values for these parameters. For simplifying the description, in the example of FIGS. 3A-C, a single parameter (SENSE factor) is used in order to be investigated or optimized. The user defines SENSE parameter values to investigate either by defining constant values or by setting a range. For subsequent measurements by the medical device using the T2-weighted MRI scan, one of the predetermined values of SENSE parameters or a value from the pre-defined range may be used. For example, the operation or use of the medical device in order to find the operational configuration may be performed by selecting different SENSE factor values for each operation of the medical device.

The operation of the medical device using for example a value of the SENSE factor may result in MR images 301. After performing the examination and producing the MR images, the user (e.g. radiologist/operator) may be asked for feedback, that may indicate a rating of the image quality of the resulting images, directly on the display device 125 that can be a console of the medical device. The user can evaluate all ratings at any time. FIG. 3B, depicts an example for user feedback interface 303 after the sequence is performed. In this example, the user is prompted to select among four different ratings namely, "excellent", "good", "moderate" and "not acceptable". It may consist of a selection on a categorical scale (e.g. excellent—good—moderate—not acceptable) as shown in FIG. 3B, a more detailed quality rating, a questionnaire asking about different quality aspects, or similar. The feedback may be stored with a link to the respective used parameter set.

Based on the feedback the SENSE factor value that has been used to produce the rated images may be maintained or rejected. For example, if the feedback indicates a "not acceptable" rate, another SENSE factor value may be used and MR images may be produced again by the medical device and the user may be asked again for feedback. This process may be repeated until the rate (e.g. "good") that is indicated in the feedback corresponds to a desired operating status of the medical device.

In one example, the medical device may be controlled to operate multiple times each time using a different SENSE factor value resulting in multiple set of MR images. In this way, after image acquisition, the user may be shown a comparable image from a comparable acquisition (e.g. same protocol and anatomy) with different parameters and asked to rate which one he likes better. The rating can be performed without giving information about the used parameters (blind review) or with parameter display (non-blind review).

In another example, for each SENSE factor value (e.g. of the two SENSE factors 1.5, 2 and 2.2 as shown in FIG. 3C), the medical device may be controlled to operate multiple times to produce respective multiple images. For each use of the medical device, the resulting images may be rated e.g. using the contrast or signal to noise ratio of the images. As shown in FIG. 3C, for the SENSE factor 1.5, the medical device has been controlled to operate 14 times, which results in 14 rates. FIG. 3C indicates that 90% of the rates are "excellent" and 10% are "good". For the SENSE factor 2.0, the medical device has been controlled to operate 17 times, which results in 17 rates. FIG. 3C indicates that 87% of the rates are "excellent", 11% are "good" and 2% are "moderate". For the SENSE factor 2.2, the medical device has been controlled to operate 15 times, which results in 15 rates. FIG. 3C indicates that 9% of the rates are "excellent", 13% are "good", 25% are "moderate" and 53% are "not acceptable".

Based on these overall ratings 311, the value of SENSE factor that provides the best overall rating may be selected or maintained. The best overall rating may automatically be selected using thresholds or may be selected by the user upon displaying the feedback interface 310.

FIG. 4 illustrates a magnetic resonance imaging system 400. The magnetic resonance imaging system 400 comprises a magnet 404. The magnet 404 is a superconducting cylindrical type magnet with a bore 406 in it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet. Such magnets may for instance be used in conjunction with charged particle beam therapy. An open magnet has two magnet sections, one above the other with a space in-between that is large enough to receive a subject 418 to be imaged, the arrangement of the two sections area similar to that of a Helmholtz coil. Inside the cryostat of the cylindrical magnet there is a collection of superconducting coils. Within the bore 406 of the cylindrical magnet 404 there is an imaging zone or volume 408 where the magnetic field is strong and uniform enough to perform magnetic resonance imaging.

Within the bore 406 of the magnet there is also a set of magnetic field gradient coils 410 which is used during acquisition of magnetic resonance data to spatially encode magnetic spins of a target volume within the imaging volume or examination volume 408 of the magnet 404. The magnetic field gradient coils 410 are connected to a magnetic field gradient coil power supply 412. The magnetic field gradient coils 410 are intended to be representative. Typically magnetic field gradient coils 410 contain three separate sets of coils for the encoding in three orthogonal spatial directions. A magnetic field gradient power supply supplies current to the magnetic field gradient coils. The current supplied to the magnetic field gradient coils 410 is controlled as a function of time and may be ramped or pulsed.

MRI system 400 further comprises an RF coil 414 at the subject 418 and adjacent to the examination volume 408 for generating RF excitation pulses. The RF coil 414 may include for example a set of surface coils or other specialized RF coils. The RF coil 414 may be used alternately for transmission of RF pulses as well as for reception of magnetic resonance signals e.g., the RF coil 414 may be implemented as a transmit array coil comprising a plurality of RF transmit coils. The RF coil 414 is connected to one or more RF amplifiers 415.

The magnetic field gradient coil power supply 412 and the RF amplifier 415 are connected to a hardware interface of control system 111. The memory 107 of control system 111 may for example comprise a control module. The control module contains computer-executable code which enables the processor 103 to control the operation and function of the magnetic resonance imaging system 400. It also enables the basic operations of the magnetic resonance imaging system 400 such as the acquisition of magnetic resonance data e.g. based on the parameters 122.

LIST OF REFERENCE NUMERALS 100 medical system
101 medical device 103 processor
107 memory
108 power supply
109 bus
111 control system
121 software
122 parameters
125 display
129 user interface
201-213 method steps
301 MR images
303 feedback interface
310 feedback interface
311 ratings
322 parameters
400 magnetic resonance imaging system
404 magnet
406 bore of magnet
408 imaging zone
410 magnetic field gradient coils
412 magnetic field gradient coil power supply
414 radio-frequency coil
415 RF amplifier
418 subject.

The invention claimed is:

1. A method for configuring medical device, the method comprising:
    providing a set of one or more para meters for configuring the medical device, each parameter of the set of one or more parameters having predefined values;
    for each patient of a plurality of patients:
        selecting from the predefined values a set of values of the set of one or more parameters, respectively;
        setting the set of one or more parameters using the selected set of values, resulting in an operational configuration of the medical device;
        controlling the medical device to operate in accordance with the operational configuration, and rating a result of the operation with regard to image quality to determine a corresponding operating status of the medical device;
        determining whether a desired operating status of the medical device can be determined based in part on the corresponding operating status of the medical device; and
        when the desired operation status cannot be determined, repeating the selecting, the setting, the controlling, and the determining fora next patient of the plurality of patients, wherein the selected set of values is different for the next patient of the plurality of patients;
        when the desired operation status can be determined, selecting the set of values of the set of one or more parameters providing a highest rating of the result of the operation; and
        operating the medical device going forward with the selected set of values.

2. The method of claim 1, wherein the controlling of the medical device results in output data of the medical device, and wherein the rating of the result of the operation comprises evaluating at least one predefined metric from the output data and comparing the evaluated at least one predefined metric with a predefined threshold.

3. The method of claim of claim 2, wherein the predefined metric comprises at least one of: processing time of the medical device for performing the operation; matching level of the output data and predefined reference data; or user rating of the output data.

4. The method of claim 1, further comprising providing a visual indication of the corresponding operating status for each patient, and receiving a user input indicative of performing the repetition.

5. The method of claim 1, wherein the repetition is performed in response to detecting a variation in the corresponding operating statuses of the plurality of patients.

6. The method of claim 1, wherein the medical device i comprises an MRI.

7. The method of claim 6, wherein the controlling of the medical device comprises acquiring MRI data and reconstructing MR images using the acquired MRI data, wherein the rating of the result of the operation with regard to quality comprises evaluating acquisition time and/or an image quality metric of the reconstructed MR images and comparing the evaluated acquisition time and/or image quality metric with predefined thresholds.

8. The method of claim 1, determining whether the desired operating status of the medical device can be determined is based on a current number of repetitions, wherein the desired operating status is obtained for a predefined number of repetitions.

9. The method of claim 1, further comprising determining the predefined values for each parameter of the set of one or more parameters, wherein the determining of the predefined values comprises:
    collecting the predefined values from one or more other medical devices similar to the medical device.

10. The method of claim 1, wherein the predefined values are user defined values.

11. The method of claim 1, wherein the selecting of the set of values is automatically performed.

12. The method of claim 1, wherein the set of parameters comprises image acquisition parameters and/or image reconstruction parameters.

13. A control system for a medical device, the control system comprising a processor, and a memory containing machine executable instructions, wherein execution of the instructions causes the processor to:
    for each patient of a plurality of patients:
        select from predefined values a set of values of a set of para meters for configuring the medical device;
        set the set of parameters using the selected set of values, respectively, resulting in an operational configuration of the medical device;
        control the medical device to operate in accordance with the operational configuration, and rate a result of the operation with regard to image quality to determine a corresponding operating status of the medical device; and
        determine whether a desired operating status of the medical device can be determined based in part on the corresponding operating status of the medical device; and
        when the desired operation status cannot be determined, repeating the selecting, the setting, the controlling, and the determining fora next patient of the plurality of patients, wherein the selected set of values is different for the next patient of the plurality of patients;
        when the desired operation status can be determined, select the set of values of the set of one or more parameters providing a highest rating of the result of the operation; and control operation of the medical device going forward with the selected set of values.

14. A non-transitory computer readable medium storing machine executable instructions for controlling a medical device, that when executed by a processor, cause the processor to:
for each patient of a plurality of patients:
select values from predefined values of a plurality of parameters, respectively, for configuring a medical device, wherein each parameter of the plurality of parameters has a plurality of predefined values;
set the plurality of parameters using the selected values, resulting in an operational configuration of the medical device;
control the medical device to operate in accordance with the operational configuration, and rate a result of the operation with regard to image quality to determine a corresponding operating status of the medical device;
determine whether a desired operating status of the medical device can be determined based in part on the corresponding operating status of the medical device; and
when the desired operation status cannot be determined, repeating the selecting, the setting, the controlling, and the determining for a next patient of the plurality of patients, wherein the selected set of values is different for the next patient of the plurality of patients;
when the desired operation status can be determined, select the set of values of the set of one or more parameters providing a highest rating of the result of the operation, and
control operation of the medical device going forward with the selected set of values.

15. The non-transitory computer readable medium of claim 14, wherein the controlling of the medical device results in output data of the medical device, and wherein the rating of the result of the operation comprises evaluating at least one predefined metric and comparing the evaluated at least one predefined metric with a predefined threshold.

16. The non-transitory computer readable medium of claim 15, wherein the metric comprises at least one of:
processing time of the medical device for performing the operation;
matching level of the output data and predefined reference data;
or user rating of the output data.

17. The method of claim 1, wherein the medical device comprises one of a CT, Ultrasound, Radiography, or PET imager.

18. The method of claim 1, further comprising determining the predefined values for each parameter of the set of one or more parameters, wherein the determining of the predefined values comprises:
theoretically determining the predefined values based on a physical model of the medical device; or
using simulation data that is obtained from a simulation of the medical device based on a model of the medical device.

19. The method of claim 1, wherein selecting the set of values of the set of one or more parameters providing the highest rating of the result of the operation comprises fitting a statistical model to the operating statuses and the selected set of values for the plurality of patients, respectively.

20. The method of claim 1, wherein determining whether the desired operating status of the medical device can be determined comprises identifying when a number of repeated iterations reaches a predefined number.

* * * * *